US006613758B1

(12) United States Patent
Bell

(10) Patent No.: US 6,613,758 B1
(45) Date of Patent: *Sep. 2, 2003

(54) METHOD FOR TREATING OSTEOPOROSIS IN CASTRATED PROSTATIC CANCER PATIENTS

(75) Inventor: Robert G. Bell, Palm Harbor, FL (US)

(73) Assignee: Barr Laboratories, Inc., Pomona, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,566

(22) Filed: Apr. 2, 1999

(51) Int. Cl.[7] ............................................... A61K 31/56
(52) U.S. Cl. ...................................... 514/179; 514/178
(58) Field of Search .................................. 514/178, 179

(56) References Cited

U.S. PATENT DOCUMENTS

| 3,234,093 A | 2/1966 | Wiechert |
| 3,895,110 A | 7/1975 | Itil et al. |
| 4,826,831 A | 5/1989 | Plunkett et al. |
| 5,135,849 A | 8/1992 | Soto et al. |
| 5,541,172 A | 7/1996 | Labrie et al. |
| 5,567,695 A | 10/1996 | Labrie |
| 5,610,150 A | 3/1997 | Labrie |
| 5,629,303 A | 5/1997 | Labrie et al. |
| 5,756,507 A | 5/1998 | Goulet et al. |

OTHER PUBLICATIONS

The Androcur Monograph, Berlex, Canada (1997).
Barradell et al., "*Cyproterone A Review of its Pharmacology and Therapeutic Efficacy in Prostate Cancer*", Drugs & Aging 5(1):59–80. (1994).
Bracci and DiSilvero, "*Present procedure with regard to the use of hormone therapy in cases of cancer of the prostate*", from Steffanine et al., Proc. 18 World Cong. International Col. Surg. Rome 1972, Excerpta Med. (AMST), from International Cong. Ser. 290:275–276 (1972).
Bruchovsky et al., "*Luteinizing Hormone–Releasing Hormone Agonists in Prostate Cancer*", Elimination of Flare Reaction by Pretreatment with Cyproterone Acetate and Low–Dose Diethylstilbestrol, Cancer 72: 1685–1691 (1993).
Claes H., et al., in Murphy GP (Prostate Cancer, Part A: Research, Endocrine Treatment, and Histopathology, New York, NY: Alan R. Liss "*Treatment of Advanced Carcinoma of the Prostate By LHRH–AGONISTS*", (1987) 229–236.
Collinson, M.P. et al., "*Osteoporosis Occurring in Two Patients Receiving LHRH Analogs for Carcinoma of the Prostate*", Calcif Tissue Int., vol. 54:327–328, (1994).
Daniell, H.W., "*Osteoporosis After Orchiectomy For Prostate Cancer*", J. Urol. 157:439–444, (1997).

El Etreby et al., "*Effect of Cyproterone Acetate in Comparison to Flutamide and Megestrol Acetate on the Ventral Prostate, Seminal Vesicle, and Adrenal Glands of Adult Male Rats*", The Prostate 11:361–375 (1987).
Goldenberg et al. "*The Combination of Cyproterone Acetate and Los Dose Diethylstilbestrol In The Treatment of Advanced Prostatic Carcinoma*", J. Urol. (1988) vol. 140: 1460–1465.
Goldenberg et al. "*Low–Dose Cyproterone Acetate Plus Mini–Dose Diethylstilbestrol–A Protocol For Reversible Medical Castration*", Urology 47 (6):882–884 (1996).
Goldenberg et al., Pharmanual 1994, "*Current Perspectives on the Expanding Role of Androcur®*" Pharma Libri Publishers Inc. 1–50.
Hinkel et al., *Cyproterone Acetate in the Treatment of Advanced Prostatic Cancer: Retrospective Analysis of Liver Toxicity in the Long–Term Follow–up of 89 Patients:*, Eur. Urol. (1996) 30:464–470.
Horan, A.H., "*Osteoporosis As A Complication Of Orchiectomy*", J. Urol. vol. 155(4):1395 (1996).
Kramer, P., et al., "*Prevention of Hot Flushes with CPA in the Hormonal Treatment of Prostatic Cancer. Results of a Placebo–Controlled Double–Blind Trial*", In: Murphy G., et al.., 3rd Int'l Symposium on Recent Advances in Urological Cancer Diagnosis and Treatment—Proceedings. Paris, France:SCI:3–7 (1992).
Krongrad, A., "*Osteoporosis After Orchiectomy For Prostate Cancer*", J. Urol. vol. 158(4):1529–30 (1997).
Loprinzi, et al., "*Megestrol Acetate For The Prevention of Hot Flashes*", N. Engl. J. Med. (1994) 331(6):347–352.
McGrath and Diamond, "*Osteoporosis As A Complication of Orchiectomy In 2 Elderly Men With Prostatic Cancer*", J Urol. vol. 154, pp. 535–536, (1995).
Physicians' Desk Reference, 35th Edition (1981), 1252–1257.
Rabe et al. "*Cyproterone Acetate Is It Hepato– or Genotoxic?*", (Drug Safety (1996(Jan.)); 14(1):25–38).
Tarle, M., "*Plasma osteocalcin values and related hormonal parameters in patients subjected to a variety of prostate anticancer agents*", Urol. Res. (1991) 19:39–44.
Watanabe, et al., "*Follow–up Study of Children with Precocious Puberty Treated with Cyproterone Acetate*", ( J. Epidemiology, vol. 7, No. 3, pp. 173–178, (1997).
Wink and Felts, "*Effects of Castration on the Bone Structure of Male Rats: A Model of Osteoporosis*", Calcif. Tissue Int. 32:77–82 (1980).

Primary Examiner—Jerome D. Goldberg
(74) Attorney, Agent, or Firm—Mark E. Waddell; Kathleen Gersh; Chadbourne & Parke LLP

(57) ABSTRACT

The present invention provides a method for preventing or treating osteoporosis in a castrated prostatic cancer patient, by administering to the patient an amount of from 10 mg to 300 mg cyproterone acetate per day. The present therapy is compatible with the patients' anti-cancer treatment.

17 Claims, No Drawings

METHOD FOR TREATING OSTEOPOROSIS IN CASTRATED PROSTATIC CANCER PATIENTS

FIELD OF THE INVENTION

The present invention relates to a treatment for slowing or preventing the progression of osteoporosis in surgically or chemically castrated prostatic cancer patients.

BACKGROUND OF THE INVENTION

Osteoporosis is generally the occurrence of a reduction in the quantity of bone, or the atrophy of skeletal tissue. This disorder is evidenced by a decrease in bone density throughout the body. Although the mechanism of osteoporosis is not entirely understood, it is believed that there is an imbalance between bone production and bone resorption, resulting in net bone resorption or breakdown. The condition can begin to occur as early as age 30. The process is typically more rapid in postmenopausal women than in men. Bone loss in males can be recognized at about 65 years of age. A significant bone loss is seen in men at about 80 years of age, and is accompanied by increased hip, spine and wrist fractures.

Surgical and chemical (e.g., LH-RH agonists) castration are widely used for the treatment of patients with prostate cancer. A number of side effects occur as a result of such therapy. Impotence and the occurrence of hot flashes are among the more distressing side effects to patients.

A less noted side effect of surgical or chemical castration is osteoporosis. It has been reported that orchiectomy for prostate cancer is often followed by severe osteoporosis (Daniell, H. W., J. Urol. 157:439–444, 1997). Castration of man and many animal species retards skeletal growth and development. Orchiectomy in rats can cause osteoporosis detectable from within two to four months. (Winks and Felts, Calcif. Tissue Res. 32:77–82 (1980); Verhas et al., Calcif. Tissue Res. 39:74–77 (1986)).

Unlike the evident side effects of orchiectomy or LH-RH agonist treatment, the pronounced onset of osteoporosis can be insidious since the risk of osteoporetic fracture increases rapidly. Moreover, these patients are preoccupied with adjusting to their treatment and addressing basic quality of life issues rather than taking measures to deter bone loss. Because of pain or their overall condition, many of these patients are not up to exercising, for instance.

It is thought that the sudden reduction in androgen levels effected by surgical castration or medical castration (e.g., LH-RH agonist treatment) in these men causes or is an important factor contributing to the degree of bone loss that can occur. (Daniell, H. W. J. Urol. 157:439–444, 1997). The correlation between the reduction in levels of adrenal estrogen in women during the menopause and the onset of osteoporosis is well known. In both sexes, the clinical situation can be described as an acquired gonadal insufficiency. Furthermore, it has been suggested that androgens increase the synthesis of bone matrix. Studies in animals have shown that testosterone administration increases the overall quantity of bone. (Silberberg and Silberberg, 1971; see Finkelstein et al., Ann. Int. Med. 106:354–361, 1987).

Estrogen replacement therapy has been the therapy of choice for osteoporosis in post-menopausal women. For men, estrogens may be effective to treat osteoporosis, but at the risk of gynecomastia and increased cardiovascular morbidity.

U.S. Pat. No. 5,541,172 to Labrie et al. addresses methods of treatment of diseases responsive to activation of the androgen receptor. The patent indicates methods for prevention and therapy of breast and endometical cancer, as well as osteoporosis. An androgenic steroid is administered such that circulating serum levels are maintained at low concentrations of between 1.0 and 50.0 nanomoles per liter. This cumulative dose is provided by administering the steroid within a sustained release formulation to avoid fluctuating blood levels.

Also discussed by the Labrie et al. patent are contentions that some synthetic progestins possess, in addition to their progesterone-like activity, varying degrees of androgenic activity. Labrie et al. indicate that progestins frequently have a high affinity for the androgen receptor at the low plasma concentrations mentioned. The patent reports on the use of medroxyprogesterone acetate and megestrol acetate. It also indicates that certain synthetic progestins or anabolic steroids including, for example, nor-testosterone, ethisterone and cyproterone acetate, possess androgenic activity at low concentrations in the in vitro system of human breast cancer ZR-75-1 cells.

The Labrie et al. patent advises assessing the specific interactions of a compound at the indicated concentrations with the androgen receptors, including estrogen, progesterone and glucocorticoid-mediated activities. At low concentrations, the compounds of interest to Labrie et al. do not interact with the glucocortioid receptor. Thus, masculinizing side effects of androgens in the treatment of women can be avoided. The patent further advises evaluating by in vitro assay the effects of a potential compound on the various receptors indicated in ZR-75-1 human breast cancer cells. The focus of the patent on the treatment of women who have diseases responsive to activation of the androgen receptor, particularly estrogen-dependent diseases, is apparent.

U.S. Pat. No. 5,567,695 to Labrie is related to the above discussed Labrie et al. patent and similarly reports a method for preventing osteoporosis. An androgenic steroid having a Ki of less than $2 \times 10^{-8}$M for the androgen receptor and having a receptor-mediated inhibitory effect on the growth of human breast cancer ZR-75-1 cells is used, where the dosage is sufficiently low to maintain a cumulative androgenic steroid serum concentration below 50 nanomoles per liter. Similar to the above Labrie et al. patent, the compounds are indicated to have the special property of potent androgenic activity at these low blood concentrations, while exhibiting little glucocorticoid activity, and therefore, they produce no visible masculinizing effects.

It has been suggested that progestational agents can potentiate bone mineralization, although the definitive effect of progesterone on bone is apparently not known. (Loprinzi, et al., N. Engl. J. Med. (1994) 331:347–352).

Cyproterone acetate ("CPA") is disclosed in U.S. Pat. No. 3,234,093, which is incorporated herein by reference. CPA, a synthetic 21-carbon hydroxyprogesterone derivative, is a steroidal antiandrogenic agent that inhibits the action of adrenal and testicular androgens on prostatic cells, resulting in total androgen blockade. Additionally, due to the antigonadotropic effects of its progestogenic activity, CPA causes a centrally mediated reduction in testicular secretion of androgens. The progestational activity of CPA is considered relatively weak. (Goldenberg, S. L. et al., Pharmanual 1994, Current Perspectives on the Expanding Role of Androcur,® Pharma Libri Publishers Inc., at p. 21).

CPA is approved for use in many countries throughout Europe, Asia, Australia, South America and Canada. It is used as a component of oral contraceptives and in the treatment of acne, seborrhea, hirsutism, precocious puberty, hypersexuality and in the treatment of prostate cancer. The pharmaceutical preparations Androcur®, Cyprostat®, Diane® and Dianette® are CPA-based products. Manufacturers of these products include Schering AG, Berlin, Germany and Berlex, Canada.

Since 1966, CPA has been used in combination with bilateral orchiectomy to achieve total androgen blockade in the treatment of prostate cancer. CPA has also been administered as monotherapy for prostate cancer. The potent antiandrogenic activity of CPA is "cancerocidal" to prostate cancer cells. Dosages of 250–300 mg/day are used to bring about a complete anti-androgenic blockade. Dosages prescribed are usually 200–300 mg/day, divided into 2–3 doses. After orchiectomy a lower daily dose of 100–200 mg may be recommended. In a study reported in 1972 by Bracci and DiSilvero (discussed in Goldenberg, S. L. et al., Pharmanual 1994, Current Perspectives on the Expanding Role of Androcur,® Pharma Libri Publishers Inc., p. 23–24), CPA was administered at 100 mg/day or more with orchiectomy to patients with various advanced tumors for more than 2 years. The investigators noted that CPA in combination with orchiectomy has marked therapeutic effectiveness.

Side effects most frequently recorded with CPA treatment relate to the hormonal effects of the drug. These include impotence, inhibition of spermatogenesis and gynecomastia. These reactions are usually reversible upon discontinuation of therapy or reduction in dose. The drug is also associated with rapid falls in serum testosterone levels, which may also produce such central nervous system effects as fatigue, weakness, and headache.

CPA has a low incidence of side effects and its antigonadotropic and antiandrogenic effects are reversible, which enables intermittent therapy. Unlike other androgen deprivation therapies, CPA is rarely associated with hot flashes. Prostate cancer patients receiving CPA combined with surgical or chemical castration are less likely to experience hot flashes than those who do not receive CPA. (Barradell et al., Drugs & Aging (1994) 5/1:59–80.)

The Androcur® Monograph, Berlex Inc., Canada (1997), indicates a general improvement in the subjective assessment of the quality of life in 70% of 367 evaluable patients participating in worldwide studies on CPA, based on criteria of general improvement in quality of life. The criteria listed are weight gain and pain relief. In a large scale randomized clinical trial on patients who had previously undergone orchiectomy and who had the mere occurrence of hot flashes and/or outbreaks of sweat, the number of patients experiencing hot flashes or outbreaks of sweating decreased after 6 months of treatment with 150 mg/day CPA (50 mg. t.i.d.). (Kramer, P., et al., In: Murphy G., et al., 3$^{rd}$ Int'l Symposium on Recent Advances in Urological Cancer Diagnosis and Treatment—Proceedings. Paris, France: SCI: 3–7 (1992)).

Another beneficial effect seen with CPA treatment has been the prevention of exacerbated bone pain. Patients with Stage C and D prostate cancer indicated improvement in bone pain with CPA as monotherapy. (Barradell et al., Drugs & Aging (1994) 5/1: 59–80). Overall, pain relief has been noted in 50–80% of patients receiving treatment with ANDROCUR®. (The Androcur Monograph, Berlex, Canada (1997)). The effect of CPA on pain generally paralleled its effect on metastasis. Id. When metastasis remained improved or stabilized, the analgesic requirement was also reduced. Id.

It has also been reported that exacerbated bone pain associated with the flare reaction at the start of LH-RH agonist treatment is prevented with CPA administered to prevent acute flare-up of prostatic disease. The Goldenberg, S. L. et al., Pharmanual (cited above), indicates that Claes H., et al., in Murphy G P (Prostate Cancer, Part A: Research, Endocrine Treatment, and Histopathology, New York, N.Y.: Alan R. Liss (1987) 229–236), found that 58.5% of 17 patients who received goserelin alone experienced a transient increase in bone pain compared with none of 7 patients who received goserelin acetate plus 200 mg/day CPA. For the short-term prevention of tumor flare, CPA has been administered with an LH-RH agonist generally at 150 to 300 mg/day dosages. Also for tumor flare, CPA has been administered at 100 mg/day in combination with 0.1 mg/day of the estrogen diethylstilbestrol (DES). (Bruchovsky et al., Cancer 71: 7282–2790 (1993)).

Dose-related hepatic toxicity in humans has been reported with the prolonged use of CPA. Toxicological studies have revealed, however, that administration of CPA to humans does not pose a serious risk of hepatotoxicity. A retrospective liver toxicity analysis was performed on 89 patients with advanced prostatic cancer who underwent orchiectomy and who received continuous additional antiandrogenic treatment with 50 mg/day CPA. (Hinkel et al., Eur. Urol. (1996) 30:464–470). CPA was administered to these patients for a period spanning from 2 to 152 months starting at the time of diagnosis. Various medications were frequently prescribed besides CPA treatment. Although a proper control group was lacking, in no case was CPA discontinued due to its side effects. After evaluating the patients' liver function, the authors concluded that CPA is a reliable drug to inhibit androgen synthesis with maximum efficacy and safety in the treatment of prostate cancer.

A review on the toxicology of CPA was published by Rabe et al. (Drug Safety (1996 (January)); 14(1):25–38). In a multi-center surveillance study of long term CPA use in over 2500 patients, the treatment group included men and women. The men were treated at dosages of either more than 200 mg/day or from 100 to 200 mg/day CPA. No correlation was found between the duration of CPA treatment and the prevalence of liver enzyme elevations. Not a single case of hepatocellular carcinoma was observed. The authors concluded that there were no observations that would indicate an increased risk of proliferative liver change as a result of CPA treatment.

The Androcur® Monograph, Berlex, Canada (1997) reports on the pharmacokinetics of CPA in humans. It indicates that the mean plasma concentration of CPA in male subjects following oral administration of one 50 mg dose is about 700 nmol/L. Continual dosing of 50 mg per day CPA would be expected to result in a plasma level of CPA maintained at an estimated concentration from about 500 to about 750 nmol/L, and upon a longer period of continual dosing, the cumulative plasma level would likely be closer to a steady state level of about 750 nmol/L or higher. Blood levels of CPA are known to be generally dose dependent.

The minimum dosage of CPA for an antigonadotropic effect in men may not be precisely known. The threshold value for an antiandrogen effect in men was indicated to be 50 mg according to U.S. Pat. No. 3,895,110, which issued in 1975. Presumably then, the threshold value for an anticancerocidal dosage in prostate cancer patients may also be 50 mg.

CPA is generally not considered an androgenic compound. In fact, CPA is therapeutically classified as an anti-androgen (Androcur® Monograph, Berlex, Canada, 1997), and is used clinically for its potent anti-androgenic activity in the treatment of prostate patients, as discussed. In a critical review of possible paradoxical androgenic activity of CPA (El Etreby et al., The Prostate 11:361–375 (1987)), the authors caution that the circumstances under which paradoxical androgen-like effects may develop are of significance. For example, inhibition of complete involution of the ventral prostate of castrated adult rats by CPA was shown to be very weak, and these results were not seen with higher doses of CPA. It was suggested that the effect may not be related to an asserted androgenicity, but rather, to an inhibitory effect on prostatic catabolic activities. The authors also explain that CPA does not meet the classical definition of an androgenic steroid "because of its inability to restore the normal size and function of adult prostates even if administered to castrated animals with involuted prostates at doses high enough and for a sufficiently long time." (El Etreby et al.)

Estrogens have a testosterone-reducing effect that is based to a large extent on the increased release of inhibitory factors from the hypothalamus in addition to a direct effect on the pituitary gland.

Goldenberg et al. (J. Urol. (1988) 140: 1460–1465) reported that CPA and low dose DES may be co-administered to achieve a synergistic androgen withdrawal effect in the treatment of advanced prostatic carcinoma. CPA administered at 200 mg/day with 0.1 mg daily DES showed a marked decrease in serum testosterone, with no change upon decreasing CPA to 100 mg/day in the combination. In a subsequent report, Goldenberg et al. (Urology 47 (6) (1996) 882–884) indicate that 100 mg CPA and 0.1 mg DES per day result in a persistent decrease in serum testosterone with a lower incidence of side effects than the 200 mg/day CPA combination. Bruchovsky et al. (Cancer 71: 2782–2790 (1993)) report elimination of flare reaction by pretreatment with CPA and low-dose DES. Patients were pretreated with 100 mg per day CPA and 0.1 mg/day DES for 4 weeks. Goserelin acetate was then given and CPA/DES was continued. DES administration was discontinued at 8 weeks to eliminate associated minor toxicity.

Goldenberg et al. (J. Urol. (1988) 140: 1460–1465) indicate that a weakening of the antigonadotropic effect of CPA, seen after 6 to 9 months, was not observed with the continued co-administration of DES.

Chlorotrianisene, an estrogen which was sold in the United States under the name TACE®, was indicated for the palliative therapy of advanced prostatic carcinoma and for moderate to severe vasomotor symptoms associated with the menopause, among other things. For long-term treatment of progressive prostatic cancer, 12 mg to 25 mg daily was prescribed. (Physicians' Desk Reference, 35th Edition (1981)).

It has also been forwarded that estrogens may increase prostatic cancer growth. In the treatment of prostate cancer, U.S. Pat. No. 5,610,150 discloses a combination therapy for prostate cancer treatment that includes an antiandrogen, a sex steroid biosynthesis inhibitor and an antiestrogen for the prevention of the biosynthesis of estrogen.

It has been reported that serum osteocalcin (OC) can be useful clinically as a marker to monitor patients with bone metastases. After testing with various anticancer treatment strategies, low dose CPA included, Tarle, M. (Urol. Res. (1991) 19:39–44) reported that OC concentration can serve as a nonspecific marker of bone lesions in patients with prostatic carcinoma. As a bone-derived protein related to mineralization processes during bone healing, elevated OC can indicate remission in patients with advanced prostatic cancer.

There is no suitable treatment for osteoporosis in surgically or chemically castrated prostatic cancer patients. A method for treating osteoporosis that is compatible with androgen ablation therapy of prostate cancer will fulfill an important medical need.

SUMMARY OF THE INVENTION

The present invention provides a method for preventing or treating osteoporosis in a castrated prostatic cancer patient, by administering to the patient an amount of from 10 mg to 300 mg cyproterone acetate per day. The present therapy is compatible with the patients' anti-cancer treatment.

DETAILED DESCRIPTION OF THE INVENTION

While androgens are generally favorable for use in the treatment of osteoporosis, androgens are contraindicated for prostatic cancer patients. Although reduced in vivo androgens are strongly correlated with the onset of osteoporosis, it is recognized that the anti-androgenic steroid cyproterone acetate is effective to treat osteoporosis in castrated prostatic cancer patients. Without wishing to be bound by any theory, it is thought that CPA, due to its progestational nature, has a positive effect on supporting bone metabolism and bone density in castrated prostatic cancer patients. Moreover, CPA is compatible with the patients' anticancer treatment.

CPA can be administered at a dosage equivalent to from 10 mg per day of a solid oral dosage form to an effective amount that is tolerated by a castrated prostatic cancer patient, for prevention or treatment of osteoporosis. For example, a dosage up to 300 mg per day solid oral CPA can be used. Preferably, lower amounts of up to 200 mg CPA per day, more preferably up to 150 mg CPA per day, are used. Preferably, the minimum dosage is 25 mg per day. Dosage amounts are preferably selected from, for instance, 25 mg, 50 mg, 100 mg and 150 mg CPA per day in a solid oral dosage form.

Castrated prostatic cancer patients, in accordance with the present invention, are those prostate cancer patients who have undergone surgical castration, e.g., bilateral orchiectomy, or who have undergone or are undergoing chemical or medical castration, e.g., by administration of an LH-RH agonist such as Lupron® or Zoladex®. These patients can additionally be undergoing or have undergone pure antiandrogen treatment such as with flutamide. The patients can be undergoing other treatments, as long as administration of CPA therewith is approved by the patients' physicians or otherwise not contraindicated.

Generally, the treatment term is for thirty days or longer, e.g., preferably at least about 180 days. Longer periods are recommended to continually deter or protect against bone loss. A period of at least 6 months, e.g., at least 9 months, is desirable. A preferred length of treatment is from 9 to 12 months. Treatment can also be for greater than 12 months. Administration can be for as long as 2 years or more, e.g., from 2 to 3 years, since CPA administered according to the present invention is well tolerated long-term. This is important because patients may survive for many years after their diagnosis.

The treatment term can be continuous or intermittent, preferably at the discretion of the physician and/or the patient under a doctor's supervision. Treatment is preferably continuous, i.e., CPA is taken every day. Continuous treatment is preferably for at least thirty days, e.g., about 180 days, more preferably for at least 6 months.

For intermittent therapy, after a period of treatment the patient withdraws from taking the drug for a length of time, and then resumes taking the drug as desired. As a guideline for intermittent treatment, the patient can take CPA continuously for more than 30 days immediately before a period during which no CPA is taken. The time during which the patient then does not take CPA generally does not exceed about 30 days. Administration is preferably continuous for at least sixty days from the start of CPA treatment and then can be intermittent at some time thereafter. Typically CPA is given continuously until PSA is at castrate levels. Withdrawal and intermittent administration, if employed, are preferably initiated after castrate levels are reached. Optimum treatment will vary from patient to patient.

The dosage is generally administered once per day, which is favorable in terms of patient compliance. Other dosage regimes such as twice or three times a day administration may be implemented. A solid oral dosage is preferably formulated as 50 mg CPA. Other dosage amounts, e.g., a 100 mg or 25 mg oral dose of CPA, may be formulated. The dosage form is preferably a tablet. Other solid dosage forms such as capsules are contemplated.

Alternatively, CPA can be provided in other dosage forms such as a liquid oral dosage, an indictable depot (solution or suspension), e.g., in a 100 mg/ml concentration, and an intranasal or a transdermal delivery system, for example, as a patch. The amount of CPA provided in each dosage form would provide equivalent blood levels of CPA as does from 10 mg to 300 mg solid oral dosage of CPA per day, preferably as does from 25 mg to 150 mg solid oral dosage form of CPA per day.

CPA therapy can begin at any time. Preferably, it begins about the time the cancer treatment begins, i.e., just before, the same time or shortly after orchiectomy or the start of treatment with the chemical castration agent. It is advantageous to begin CPA treatment early to offset loss of bone. Other beneficial effects may also occur, e.g., an additional anticancerocidal effect, alleviation of tumor flare and prevention of hot flashes.

CPA can be used in accordance with the present invention to treat castrated prostatic cancer patients having any stage of prostatic cancer to deter or treat osteoporosis.

It is also recognized that CPA in combination with a low dose estrogen is useful in treating castrated prostatic cancer patients for osteoporosis. Moreover, the combination can have a synergistic effect on the treatment of osteoporosis. The lowest synergistically effective dosage of estrogen is preferred in order to minimize undesirable side effects. The estrogen can be administered every day or on alternate days.

A preferred estrogen of the combination is DES. Dosages in accordance with the present invention are from 10 mg to 300 mg CPA, preferably 25 mg to 150 mg CPA, combined with about 0.01 mg to about 3 mg DES per day or every other day. Preferred dosages are from 50 mg CPA to 100 mg CPA per day in combination with 0.01 mg to 0.1 mg DES per day or every other day. The optimum treatment dosage with minimum undesirable side effects can vary from patient to patient.

It is also recognized that CPA can be used in combination with the estrogen chlorotrianisene to treat castrated prostatic cancer patients for osteoporosis. Dosages in accordance with the present combination are from 10 mg to 300 mg CPA, preferably 25 mg to 150 mg CPA combined with from about 0.1 mg to about 25 mg chlorotrianisene per day. It is recognized that from 0.1 mg up to 12 mg chlorotrianisene in combination with CPA is effective in the treatment of osteoporosis. Dosages of 50 mg CPA to 100 mg CPA in the combination are more preferable. It is recognized that the combination with chlorotrianisene provides an effective treatment with low associated toxicity.

Other estrogens can be used. Naturally derived estrogens such as the conjugated estrogens in Premarin® may be administered. Synthetic conjugated estrogens such as ethinyl estradiol, quinestranol and mestranol may also be used. Further examples of estrogens are estradiol, estradiol valerate, piperazine estrone sulphate, estrone, estriol, estriol succinate and polyestriol phosphate.

Treatment duration, dosage forms and other parameters discussed above for CPA alone are applicable. A combination formulation of CPA with a low dose estrogen can be administered as a combined formulation or as two separate dosage units.

Castrated prostatic cancer patients undergoing treatment with CPA in accordance with the present invention can begin taking a low dose estrogen with their CPA therapy at any time. Commencing combination therapy prior to six months from the start of CPA administration may be particularly beneficial as it could alleviate any potential weakening of the antigonadotropic effect of CPA.

Typical clinical measurements to determine osteoporosis use specialized x-ray machines that measure a patient's hip or spine. To assess a patient's bone mineral density, bone density measurements can be made by absorptiometry (single/dual photon absorptiometry, single/dual x-ray photon absorptiometry and dual-energy quantitative computerized tomography). The measurement preferably can be made at two points of the arm ($\frac{1}{3}$ and $\frac{1}{10}$ of the forearm length from a distal end of the radius). Studies have shown that measuring heel density can also accurately predict osteoporosis. A newer device, the Sahara Clinical Bone Sonometer, uses ultrasound to assess a patients' bones by measurement of heel density.

Other markers can be used to assess bone absorption and/or resorption. (Reginste et al., 1993, Genant et al., 1996). Plasma and urinary calcium and phosphate levels, plasma alkaline phosphatase, calcitonin and parathormone concentrations, as well as urinary hydroxyproline and calcium/creatinine ratios are some of these markers. Both traditional (urinary calcium/creatinine and hydroxyproline/creatinine) and currently used specific (urinary pyridinoline/creatinine and deoxypyridinoline/creatinine) markers of bone resorption can be used. Development of specific and sensitive assays to measure biochemical markers reflecting the overall rate of bone formation and bone resorption has markedly improved the non-invasive assessment of bone turnover in various metabolic bone diseases, especially osteoporosis. Human osteocalcin and bone alkaline phosphatase as markers are measured by what may be the most sensitive means to assess bone formation. Immunoassays are available to the intact osteocalcin molecule as well as its major proteolytic fragment, and to bone alkaline phosphatase. For bone resorption, the total urinary excretion of pyridinoline crosslinks measured by high pressure liquid chromatography has shown its superiority over all other markers for the clinical assessment of osteoporosis. The recent development of immunoassays recognizing either the free pyridinoline crosslinks or pyridinoline crosslinked-type I collagen peptides in urine and serum should allow a broad use of this sensitive resorption marker.

As the clinician is aware, bone density can vary widely even among people with healthy bone. In assessing whether any patient has an increased risk of developing osteoporosis, or has developed osteoporosis, risk factors such as whether the patient is a smoker or is small-framed should be considered. The targeted group of patients, castrated prostatic cancer patients, are considered to have a high risk of osteoporosis. A determination of bone density is preferably made prior to the surgical or chemical castration treatment to obtain an indication of the state of the patients' bones before this risk factor is introduced, for comparative purposes.

From the foregoing description, one skilled in the art can ascertain the essential characteristics of this invention, and without departing from the spirit and scope thereof, can make various changes and modifications. Preferred embodiments set forth by way of illustration are not intended as limitations on the variations possible in practicing the present invention.

What is claimed is:

1. A method for preventing or treating osteoporosis in a castrated prostatic cancer patient in reed thereof, comprising administering to said patient an amount of from 50 mg to 300 mg cyproterone acetate per day.

2. The method according to claim 1 wherein the administering is continuous.

3. The method according to claim 1 wherein the administering is continuous for at least sixty days from the start of administration and intermittent thereafter.

4. The method according to claim 1 wherein the administering is for at least about 30 days.

5. The method according to claim 1 wherein the administering is for at least about 6 months.

6. The method according to claim 5 wherein the administering is for from about 6 months to about 9 months.

7. The method according to claim 1 wherein the administering is for at least about 9 months.

8. The method according to claim 1 wherein the administering is for over 1 year.

9. The method according to claim 1 wherein the administering is for at least about 2 years.

10. The method according to claim 9 wherein the administering is for from about 2 to about 3 years.

11. The method according to claim 1 wherein the amount is from 50 mg to 150 mg cyproterone acetate per day.

12. The method according to claim 11 wherein the administering is for at least about 6 months.

13. The method according to claim 11 wherein the administering is for greater than one year.

14. The method according to claim 1 wherein the amount is from 50 mg to 100 mg cyproterone acetate per day.

15. The method according to claim 1 wherein the patient is a chemically castrated prostatic cancer patient.

16. The method according to claim 1 wherein the patient is an orchiectomized prostatic cancer patient.

17. The method according to claim 1 wherein the administering is once per day.

* * * * *